United States Patent
Suga et al.

(10) Patent No.: US 9,847,444 B2
(45) Date of Patent: Dec. 19, 2017

(54) PHOTONIC DEVICE AND OPTICAL COHERENCE TOMOGRAPHY APPARATUS INCLUDING THE PHOTONIC DEVICE AS LIGHT SOURCE

(71) Applicant: CANON KABUSHIKI KAISHA, Tokyo (JP)

(72) Inventors: Takako Suga, Yokohama (JP); Takeshi Uchida, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 341 days.

(21) Appl. No.: 14/438,121

(22) PCT Filed: Oct. 30, 2013

(86) PCT No.: PCT/JP2013/080054
§ 371 (c)(1),
(2) Date: Apr. 23, 2015

(87) PCT Pub. No.: WO2014/073583
PCT Pub. Date: May 15, 2014

(65) Prior Publication Data
US 2015/0295126 A1  Oct. 15, 2015

(30) Foreign Application Priority Data
Nov. 6, 2012  (JP) .................................. 2012-244344

(51) Int. Cl.
*H01L 33/22*  (2010.01)
*H01L 33/00*  (2010.01)
(Continued)

(52) U.S. Cl.
CPC ...... *H01L 33/0045* (2013.01); *G01B 9/02091* (2013.01); *G01N 21/4795* (2013.01);
(Continued)

(58) Field of Classification Search
CPC ......... H01L 33/22; H01L 33/20; H01L 33/38; H01L 33/008
See application file for complete search history.

(56) References Cited

U.S. PATENT DOCUMENTS 5,226,053 A     7/1993  Cho et al.
7,851,813 B2 *  12/2010 Kim ........................ H01L 33/06
                                                          257/88
(Continued)

FOREIGN PATENT DOCUMENTS

JP  H05-275739 A  10/1993
JP  H09-172197 A   6/1997
(Continued)

OTHER PUBLICATIONS

International Search Report and Written Opinion of the International Searching Authority issued in corresponding application No. PCT/JP2013/080054 dated Feb. 10, 2014 (7 pages).

*Primary Examiner* — Quoc Hoang
(74) *Attorney, Agent, or Firm* — Fitzpatrick, Cella, Harper & Scinto

(57) ABSTRACT

Provided is a photonic device in which emission intensity in a short wavelength region is suppressed even in the case of increasing carrier injection density so as to obtain a wide spectrum half-maximum width as well as a high output. The photonic device includes: a first cladding layer; a second cladding layer; and an active layer including an emitting layer and a barrier layer and being provided between the first cladding layer and the second cladding layer, the emitting layer emitting light in a spectrum having a center wavelength $\lambda c$ and a spectrum half-maximum width $\Delta\lambda$, in which at least one of the first cladding layer and the second cladding layer includes a light absorbing part for absorbing light having a wavelength of $\lambda s$ or less represented by the following Expression (1):

$$\lambda s < (\lambda c - (\Delta\lambda/2)) \qquad (1).$$

12 Claims, 11 Drawing Sheets

(51) Int. Cl.
  *G01B 9/02* (2006.01)
  *H01L 33/08* (2010.01)
  *G01N 21/47* (2006.01)
  *H01L 33/06* (2010.01)
  *H01L 33/14* (2010.01)

(52) U.S. Cl.
  CPC .............. *H01L 33/06* (2013.01); *H01L 33/08* (2013.01); *H01L 33/14* (2013.01)

(56) References Cited

U.S. PATENT DOCUMENTS 7,957,442 B2* 6/2011 Hashimoto ............ B82Y 20/00
  372/43.01
2004/0065890 A1 4/2004 Alphonse et al.

FOREIGN PATENT DOCUMENTS

| JP | 2007-208062 A | 8/2007 |
| JP | 2007-227801 A | 9/2007 |
| JP | 2012-069770 A | 4/2012 |
| JP | 2012-160665 A | 8/2012 |

* cited by examiner

PHOTONIC DEVICE AND OPTICAL COHERENCE TOMOGRAPHY APPARATUS INCLUDING THE PHOTONIC DEVICE AS LIGHT SOURCE

TECHNICAL FIELD

The present invention relates to a photonic device, and an optical coherence tomography apparatus including the photonic device as a light source.

BACKGROUND ART

In recent years, a super luminescent diode (hereinafter referred to as "SLD") is drawing attention.
The SLD differs from a semiconductor laser and a light emitting diode (LED). The semiconductor laser oscillates light having a high output power and a very narrow spectrum width with a low injection current through stimulated emission and further resonation of the light. The LED has a wide radiation angle using spontaneous emission light.

Specifically, in the SLD, there is such a feature that a high output power and a wide spectrum half-maximum width are obtained by employing a configuration of not resonating light even in a high current injection state while the light induced amplification is used.
Through use of those features, applications of the SLD have been expanded into various fields, such as a spectroscope, a length measuring instrument, a refractive-index distribution measuring apparatus, a tomography apparatus, and a light source for excitation.

As described above, in order to realize a particularly wide spectrum half-maximum width, in the SLD, high current injection is needed to operate a device compared to that of a semiconductor laser.
The characteristics of light emission of the SLD are described below with reference to FIGS. 2A to 2C.
FIG. 2A shows spectrum intensity in the case of using a single quantum well in a layer for emitting light (hereinafter abbreviated as "SQW").
In FIG. 2A, a horizontal axis represents a wavelength, and a vertical axis represents spectrum intensity. Multiple spectrum waveforms correspond to different injection current level.
In FIG. 2A, when a spectrum waveform 201 at a time of lowest injection current is compared to a spectrum waveform 202 at a time of highest injection current, intensity of an emission wavelength at a high-order level (represented by an dotted arrow 203) increases and a spectrum half-maximum width is enlarged along with an increase in injection current.
In this case, a spectrum shape changes in such a manner that a change on a long wavelength side is small, and intensity on a short wavelength side increases along with high injection current.

Next, FIGS. 2B and 2C show the case of using multi quantum wells in a layer for emitting light (hereinafter abbreviated as "MQW").
FIG. 2B shows a band diagram on a conduction band side of two quantum wells having the same composition and different thicknesses. Black points represent electrons serving as carriers.
A quantum well 204 has a thickness smaller than that of a quantum well 205. Therefore, the quantum well 204 has a bandgap larger than that of the quantum well 205 owing to a quantum effect and is capable of emitting light having a short wavelength.
FIG. 2C shows gains corresponding to the respective quantum wells.
At a time of low injection current, electrons are accumulated in the quantum well 205 to emit light. When the injection current is increased, electrons are also accumulated in the quantum well 204 to emit light. At the same time, light is also emitted from an energy position higher than that of the quantum well 205, and hence the shape of a gain from the quantum well 205 changes from a form indicated by a solid line 207 to that indicated by a dotted line 208. Consequently, the intensity on a short wavelength side further increases (dotted arrow 209). As described above, irrespective of whether the SQW or the MQW is used, when the spectrum half-maximum width is enlarged, there occurs such a phenomenon that the intensity on a short wavelength side increases further compared to that on a long wavelength side, which is a feature of the SLD.

The light on a short wavelength side may cause the following problems in terms of use.
That is, light having a short wavelength has high energy, and hence may damage a measurement system or an object to be measured depending on the wavelength.

Further, an increase in intensity caused by an increase in injection current is significant. Therefore, depending on the injection current, a spectrum half-maximum width rather becomes narrower, i.e., a spectrum shape is greatly deviated from a Gaussian shape, which may cause noise during measurement.

In particular, in the case of using the SLD as a light source for fundus OCT (optical coherence tomography), when light having a wavelength of 790 nm or less enters an eyeball, the luminosity factor is enhanced to cause the contraction of a pupil. Therefore, it becomes difficult to perform correct measurement.

Conventionally, as a method of suppressing an output on a short wavelength side, Patent Literature 1 proposes a semiconductor laser element described below.

FIGS. 11A to 11D show gain shapes and spectrum shapes of semiconductor laser elements according to a conventional example and an example described in Patent Literature 1. FIGS. 11A and 11B show the conventional example, and FIGS. 11C and 11D show the example of Patent Literature 1. FIGS. 11A and 11C show gain spectra 41 and light absorption spectra 42, and FIGS. 11B and 11D show an oscillation spectrum 45 of the conventional example and an oscillation spectrum 46 of the example described in Patent Literature 1, respectively. Further, FIG. 12 is a band diagram showing one configuration of the vicinity of an active layer in the semiconductor laser element according to the example of Patent Literature 1.

The semiconductor laser element of Patent Literature 1 has a configuration in which a light absorbing layer 14 and a separation layer 15 are arranged between a barrier layer 32 and a cladding layer 13 in a Fabry-Perot laser.

CITATION LIST

Patent Literature

PTL 1: Japanese Patent Application Laid-Open No. 2007-208062

SUMMARY OF INVENTION

Technical Problem

The Fabry-Perot laser described in Patent Literature 1 is driven at a current lower than that of the SLD, and hence the carrier density during driving in the Fabry-Perot laser is lower than that of the SLD. Therefore, with the thickness of the separation layer 15 described in Patent Literature 1, the carriers can be prevented from entering the light absorbing layer 14.

However, the SLD intended by the present invention basically has a mechanism for emitting light, which is different from that of the Fabry-Perot laser, and in order to obtain a wide spectrum half-maximum width as well as a high output, the SLD requires carrier density higher than that of the Fabry-Perot laser.

Thus, in the case where the configuration described in Patent Literature 1 is used, carriers cannot be blocked from entering a light absorbing layer, and hence the carriers are injected into the light absorbing layer. Then, the light absorbing layer does not absorb light, and further the light absorbing layer may emit light in some cases. Therefore, in the configuration described in Patent Literature 1, in the case where injection density of carriers is increased so as to obtain a wide spectrum half-maximum width as well as a high output, light intensity on a short wavelength side increases, with the result that the above-mentioned problem in that a measurement system or an object to be measured is damaged cannot be solved.

Solution to Problem

The present invention has been achieved in view of the above-mentioned problem, and it is an object of the present invention to provide a photonic device in which emission intensity in a short wavelength region is suppressed even in the case of increasing carrier injection density so as to obtain a wide spectrum half-maximum width as well as a high output.

According to one embodiment of the present invention, there is provided a photonic device, including: a first cladding layer; a second cladding layer; and an active layer including an emitting layer and a barrier layer and being provided between the first cladding layer and the second cladding layer, the emitting layer emitting light in a spectrum having a center wavelength λc and a spectrum half-maximum width Δλ, in which at least one of the first cladding layer and the second cladding layer includes a light absorbing part for absorbing light having a wavelength of λs or less represented by the following Expression (1).

$$\lambda s < (\lambda c - (\Delta\lambda/2)) \quad (1)$$

Further, according to one embodiment of the present invention, there is provided an optical coherence tomography apparatus, including: a light source part including the photonic device described above; an analyte measuring part for irradiating an analyte with light from the light source part and transmitting reflected light from the analyte; a reference part for irradiating a reference mirror with the light from the light source part and transmitting reflected light from the reference mirror; an interference part for causing reflected light from the analyte measuring part and reflected light from the reference part to interfere with each other; a light detecting part for detecting interference light from the interference part; and an image processing part for obtaining a tomographic image of the analyte based on the interference light detected by the light detecting part.

Further features of the present invention will become apparent from the following description of exemplary embodiments with reference to the attached drawings.

DESCRIPTION OF EMBODIMENTS

Preferred embodiments of the present invention will now be described in detail in accordance with the accompanying drawings.

A photonic device according to an embodiment of the present invention includes a first cladding layer, a second cladding layer, and an active layer including an emitting layer and a barrier layer provided between the first and second cladding layers, in which a spectrum of light emitted from the emitting layer has a center wavelength λc and a spectrum half-maximum width Δλ. At least one of the first cladding layer and the second cladding layer includes a light absorbing part for absorbing light having a wavelength of λs represented by the following expression (1).

$$\lambda s < (\lambda c - (\Delta\lambda/2)) \quad (1)$$

In the following, a super luminescent diode (SLD) which is an example of the photonic device is described.

The SLD has a configuration in which the light absorbing part for decreasing intensity only on a short wavelength side without changing a half-maximum width of an emission spectrum of the emitting layer vertically sandwiched between the barrier layers is disposed in an n- or p-doped cladding layer. Specifically, the SLD according to the embodiment has a configuration illustrated in FIG. 1.

Figure 1:
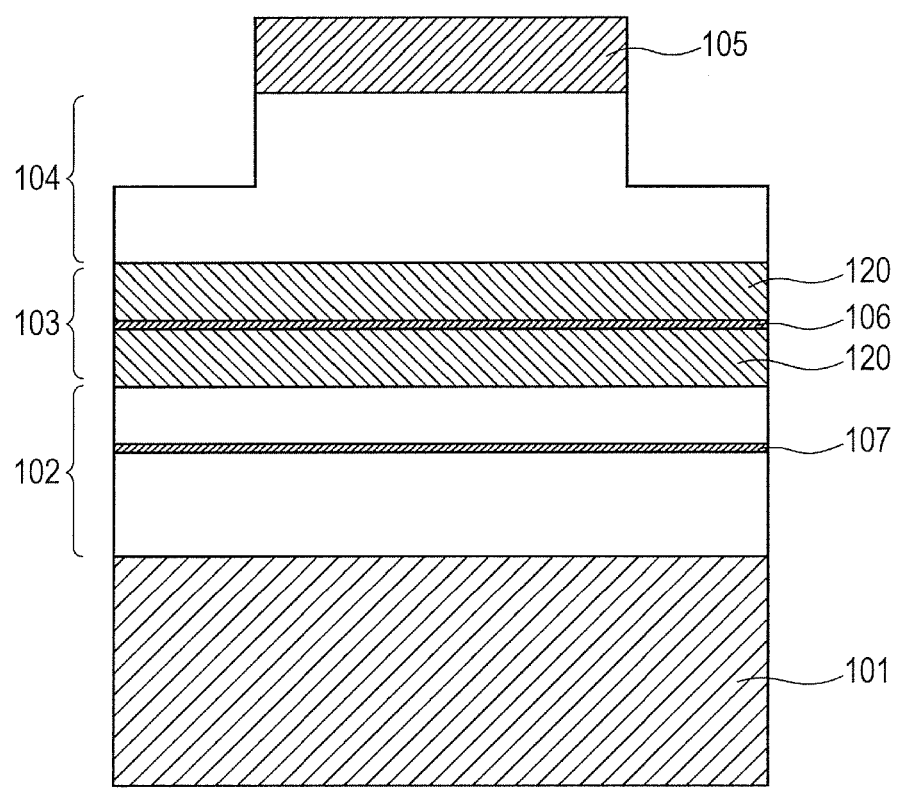
FIG. 1 is a view illustrating an exemplary configuration of an SLD according to an embodiment of the present invention.
Figure 2A:
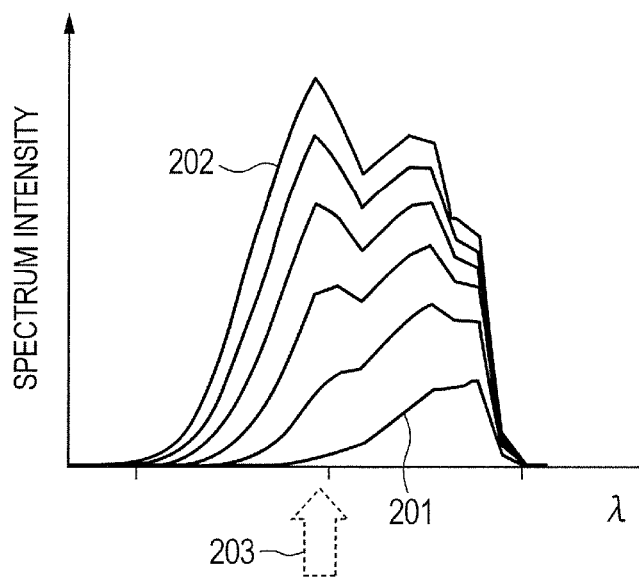
FIG. 2A is a graph showing a problem of the present invention.
Figure 2B:
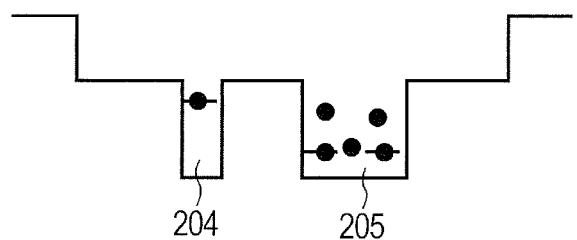
FIG. 2B is a band diagram showing the problem of the present invention.
Figure 2C:
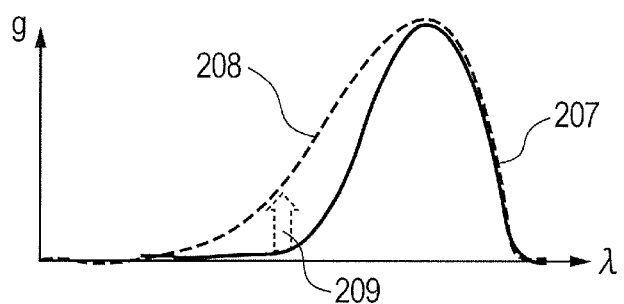
FIG. 2C is a graph showing the problem of the present invention.

That is, as illustrated in FIG. 1, an n- or p-doped lower cladding layer (first cladding layer) 102 is provided on a substrate 101.

A non-doped active layer 103 including an emitting layer 106 and barrier layers 120 is provided on the lower cladding layer 102, and a p- or n-doped upper cladding layer (second cladding layer) 104 is provided on the active layer 103. Then, a contact layer 105 is provided on the upper cladding layer 104.

Further, electrodes are provided in a lower portion of the substrate 101 and an upper portion of the contact layer 105, respectively (not shown). The contact layer 105 and part of the upper cladding layer 104 are formed in a ridge shape.

In either one or both of the upper cladding layer 104 and the lower cladding layer 102, a light absorbing layer 107 is disposed. The light absorbing layer 107 absorbs light having a wavelength not more than $\lambda s$ satisfying the following expression (1), of the light from the emitting layer 106.

$$\lambda s < (\lambda c - (\Delta \lambda / 2)) \quad (1)$$

provided that: $\lambda c$ represents a spectrum center wavelength of light emitted from the emitting layer 106, and $\Delta \lambda$ represents a spectrum half-maximum width.

Note that, FIG. 1 illustrates an example in which the light absorbing part 107 is provided only in the lower cladding layer 102. Further, in the SLD according to this embodiment, it is desired that the spectrum center wavelength of light emitted from the emitting layer 106 be set in a range of 830 to 870 nm.

The above-mentioned expression (1) is described with reference to FIG. 3.

Figure 3:
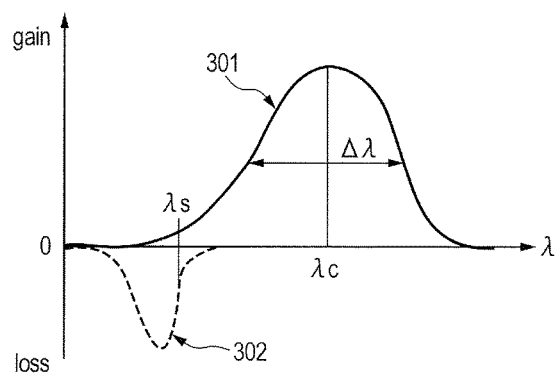
FIG. 3 is a graph showing a relationship between a wavelength and a gain of the SLD according to the embodiment of the present invention.

In FIG. 3, a horizontal axis represents a wavelength, and a vertical axis represents a gain. In a gain spectrum 301 of the emitting layer 106, a center wavelength of the spectrum half-maximum width $\Delta \lambda$ is defined as the spectrum center wavelength $\lambda c$.

A dotted line represents a gain spectrum 302 of the light absorbing part 107. The light absorbing part 107 is adjusted for a composition, a thickness, an arrangement position, and the like so that a loss is obtained at the wavelength of $\lambda s$ or less which corresponds to a region in which light intensity is intended to be decreased. With such a configuration, light emission in a short wavelength region is suppressed. Note that, it seems that more satisfactory absorption effect is obtained by disposing the light absorbing part 107 in the vicinity of the emitting layer 106, that is, in the non-doped active layer 103. However, carriers are also likely to be injected into the light absorbing part 107 simultaneously, with the result that light is emitted from the light absorbing part 107.

Thus, it is preferred that the light absorbing part 107 be disposed in the doped cladding layer and be disposed at a position where intensity of light emitted from the emitting layer 106 is not likely to decrease so that carrier injection is minimized.

In the case where the lower cladding layer 102 is a doped cladding layer, it is preferred that the doping concentration of layers (not shown) on the periphery of the light absorbing part 107 disposed in the cladding layer 102 be lower than that of layers (not shown) adjacent to the layers on the periphery of the light absorbing part 107. The reason for this is as follows. In the case where the light absorbing part 107 includes a quantum well layer, a gain spectrum of the quantum well layer is changed depending on the doping amount of the layers on the periphery of the light absorbing part 107. When the doping amount of the layers on the periphery of the light absorbing part 107 is increased, the gain spectrum takes a blunt shape, and a loss region becomes broad. On the other hand, when the doping concentration of the layers on the periphery of the light absorbing part 107 is decreased, the gain spectrum takes a more acute shape on a short wavelength side, which can effectively decrease the intensity at a desired wavelength or less.

When the thickness of the layers on the periphery of the light absorbing part 107 is too small, the effect of a change in gain spectrum becomes small, and when the thickness thereof is too large, the flow of carriers is influenced. Therefore, it is preferred that the layers on the periphery of the light absorbing part 107 extend upward and downward by about 20 nm from the light absorbing part 107 to a region adjacent to the light absorbing part 107, although it depends on the configuration of the SLD. Further, as the doping concentration of the layers on the periphery of the light absorbing part 107 becomes lower than that of the layers adjacent to the layers on the periphery of the light absorbing part 107, the effect of a change in gain spectrum is larger. However, when the doping concentration of the layers on the periphery of the light absorbing part 107 is too low, the flow of carriers is influenced, and hence, the doping concentration of the layers on the periphery of the light absorbing part 107 is preferably 1/10 or less, in particular 1/10 or less and 1/1000 or more of that of the layers adjacent to the layers on the periphery of the light absorbing part 107.

Specific examples are described in more detail with reference to FIGS. 4A and 4B.

Figure 4A:
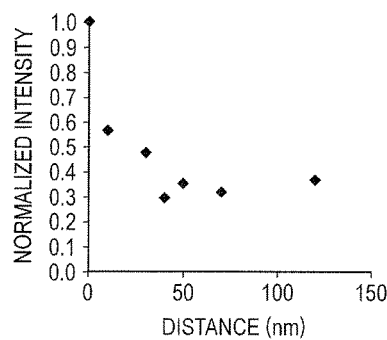
FIG. 4A is a graph showing normalized intensity with respect to a position of a light absorbing layer.
Figure 4B:
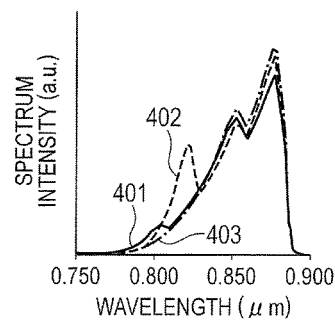
FIG. 4B is a graph showing a spectrum shape with respect to the position of the light absorbing layer.

FIGS. 4A and 4B are graphs showing the dependence of a spectrum shape and absorption effect on the position where the light absorbing part 107 is disposed in the example of the SLD illustrated in FIG. 1.

The SLD shown in FIGS. 4A and 4B is specifically configured as follows.

The substrate 101 is a GaAs substrate. The lower cladding layer 102 is made of n-doped $Al_{0.5}GaAs$. The active layer 103 includes the emitting layer 106 made of $In_{0.07}GaAs$ and the barrier layers 120 made of $Al_{0.2}GaAs$.

Further, the upper cladding layer 104 is made of p-doped $Al_{0.5}GaAs$, and the upper contact layer 105 is made of p-doped GaAs.

The thickness of the active layer 103 is set to 48 nm, and the thickness of the emitting layer 106 is set to 8 nm. The emitting layer 106 is disposed at the middle of the active layer 103. As the light absorbing part 107, a GaAs layer having a thickness of 5 nm is used, and FIGS. 4A and 4B show the results obtained by changing the distance from the emitting layer 106 to the light absorbing part 107.

In FIG. 4A, a horizontal axis represents a distance from the emitting layer 106 to the light absorbing part 107 in the p-side direction, and a vertical axis represents normalized intensity when the intensity at a wavelength of 790 nm in the absence of the light absorbing part 107 is defined as 1.

In this case, zero distance corresponds to the case where the light absorbing layer 107 is not provided (this is because the emitting layer 106 and the light absorbing layer 107 cannot be arranged at the same position). The distance up to 20 nm corresponds to the case where the light absorbing layer 107 is disposed in the non-doped active layer 103, and the distance of 20 nm or more corresponds to the case where the light absorbing layer 107 is disposed in the doped upper cladding layer 104.

In a case where the normalized intensity is smaller than 1, it is indicated that the light absorbing layer 107 is absorbing light.

As is understood from FIG. 4A, the light absorbing part 107 absorbs light even when the light absorbing part 107 is disposed (at a distance of 10 nm from the emitting layer 106) in the non-doped active layer 103. The normalized intensity becomes minimum at a distance of about 40 to 70 nm from the emitting layer 106, and when the distance is further increased, the normalized intensity increases, that is, the absorption by the light absorbing part 107 decreases.

FIG. 4B shows three kinds of spectrum shapes.

Compared to a solid line 401 representing a spectrum shape of only the emitting layer 106 (the case where the light absorbing part 107 is not provided), in a dotted line 402 representing the case where the light absorbing part 107 is disposed in the non-doped barrier layer (at a distance of 15 nm from the emitting layer 106), the intensity at a wavelength of 790 nm or less decreases. However, a peak is newly formed in a spectrum shape in the vicinity of a wavelength of 820 nm, and thus the spectrum shape greatly changes.

The peak in the vicinity of the wavelength of 820 nm is considered as a peak formed by light emission caused by the injection of carriers into the light absorbing part 107.

When the spectrum shape is greatly deviated from the Gaussian shape as in the dotted line 402, inconvenience may occur, in which intensity of a noise component appears due to the peak from a short wavelength, etc.

On the other hand, in an alternate long and short dash line 403 representing the case where the light absorbing part 107 is disposed in the doped cladding layer (at a distance of 30 nm from the emitting layer 106), only the intensity at a wavelength of 790 nm or less decreases. Thus, no substantial difference in a spectrum shape on a long wavelength side is found, compared to the solid line 401 representing the original spectrum shape.

Although not shown in FIG. 4B, no substantial difference in the spectrum shape is found even when the distance is further increased.

It is understood from FIG. 4A that, as the distance increases, the normalized intensity decreases (absorption increases), but increases again after reaching a minimum value.

Figure 5:
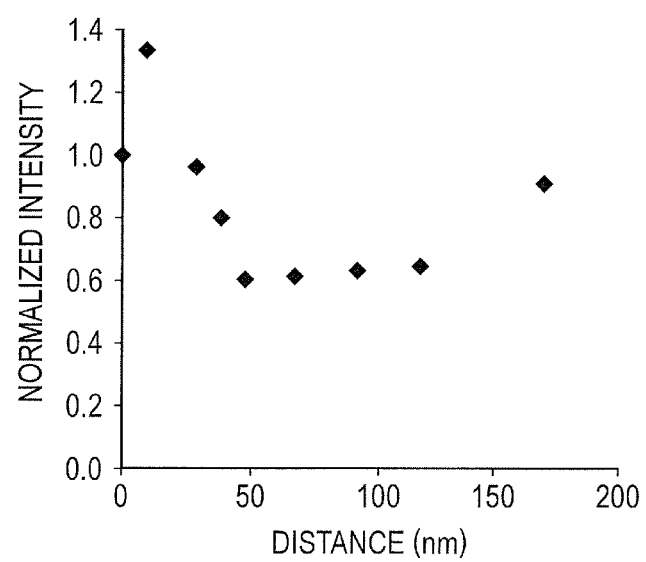
FIG. 5 is a graph showing normalized intensity with respect to the position of the light absorbing layer.

FIG. 5 shows the results similar to those of FIGS. 4A and 4B, except that the light absorbing part 107 is made of GaAs and has a thickness of 6 nm, and the light absorbing part 107 is disposed on the n-side with respect to the emitting layer 106.

When the light absorbing part 107 is disposed in the non-doped active layer 103, the normalized intensity exceeds 1.

The reason for this is considered as follows. Carriers are injected into the light absorbing part 107, and the light absorbing part 107 emits light. It is understood that, when the light absorbing part 107 is disposed in the doped lower cladding layer 102 (at a distance of 20 nm or more from the emitting layer 106), the normalized intensity becomes less than 1, and light of the intensity at a wavelength of 790 nm is absorbed.

The normalized intensity reaches a minimum value in the vicinity of a distance of 50 nm and increases (absorption decreases) when the distance is further increased.

There are some differences in characteristics due to the difference in a waveguide structure or the like, caused by the thickness and composition of the light absorbing layer 107, whether the light absorbing layer 107 is disposed on the p-side or the n-side with respect to the emitting layer 106, the thickness of the active layer 103, and a refractive index difference between the active layer 103 and the cladding layer. However, in any case, when the light absorbing layer 107 is disposed in the non-doped active layer 103, the following inconveniences occur. The spectrum shape greatly changes, and light is also emitted on a short wavelength side.

Thus, the light absorbing layer 107 needs to be disposed in the doped cladding layer.

The number of the light absorbing parts 107 is not limited to one and can be adjusted depending on the light amount intended to be decreased. In particular, in the case where the volume of the emitting layer 106 is large, a loss amount in the light absorbing part 107 may become insufficient in some cases. In this case, multiple light absorbing parts 107 may be used.

Further, the light absorbing part 107 may be disposed not only in the cladding layer on one side but also in the cladding layers on both sides.

As described above, by disposing the light absorbing part 107 at an appropriate distance from the non-doped region, minority carriers which overflow the non-doped region can be prevented from reaching and flowing into the light absorbing part 107.

Meanwhile, the SLD is driven at carrier density higher than that for general laser diodes, and hence the amount of overflowing minority carriers is also larger. Therefore, depending on the structure and drive conditions of the active layer of the SLD, more specifically, the current density and the temperature of the active layer, carriers cannot be sufficiently suppressed merely with the above-mentioned measures, and hence light is emitted from the light absorbing layer in some cases.

In the above-mentioned case, carriers can be suppressed more preferably by providing a layer having a bandgap smaller than that of the cladding layer or a layer having a bandgap larger than that of the cladding layer between the light absorbing layer and the non-doped region. In the case of providing both of those layers, it is most preferred that the layer having a bandgap smaller than that of the cladding layer and the layer having a bandgap larger than that of the cladding layer be provided in the stated order from the side close to the non-doped region.

For example, the configuration is assumed in which the emitting layer 106 includes multiple semiconductor layers and at least either one of the first cladding layer 102 and the second cladding layer 104 is doped. In this configuration, a carrier consuming layer is provided, which has a bandgap smaller than those of the first and second cladding layers 102 and 104 and larger than that of a layer having the smallest bandgap among the multiple semiconductor layers. The carrier consuming layer is provided in the doped cladding layer between the emitting layer 106 and the light absorbing layer 107.

Further, the carrier consuming layer and a barrier layer having a bandgap larger than that of the doped cladding layer are located in the doped cladding layer between the emitting layer 106 and the light absorbing layer 107, and the active layer 103, the carrier consuming layer, and the barrier layer are provided in the stated order.

A specific example thereof is shown in Example 5.

The case where the emitting layer 106 uses a quantum well is described above as a specific example. However, the present invention is not limited thereto, and the emitting layer 106 may be any of a bulk, a quantum well, a quantum wire, and a quantum dot as long as light is emitted from a high energy position due to an increase in injection current.

Further, although the case of using a quantum well also as the light absorbing layer 107 is described, the present invention is not limited thereto, and the light absorbing layer 107 may be any of a bulk, a quantum well, a quantum wire, and a quantum dot as long as the light absorbing layer has a loss in a wavelength band at a desired wavelength or less.

An absorption peak on a short wavelength side becomes more acute by using a quantum well, a quantum wire, or a quantum dot instead of a bulk for the light absorbing layer 107.

Next, an exemplary configuration of an optical coherence tomography apparatus (hereinafter sometimes referred to as "OCT apparatus") is described, which includes, as a light source part, an SLD using quantum wells (typical example) for an emitting layer and a light absorbing layer.

Figure 10:
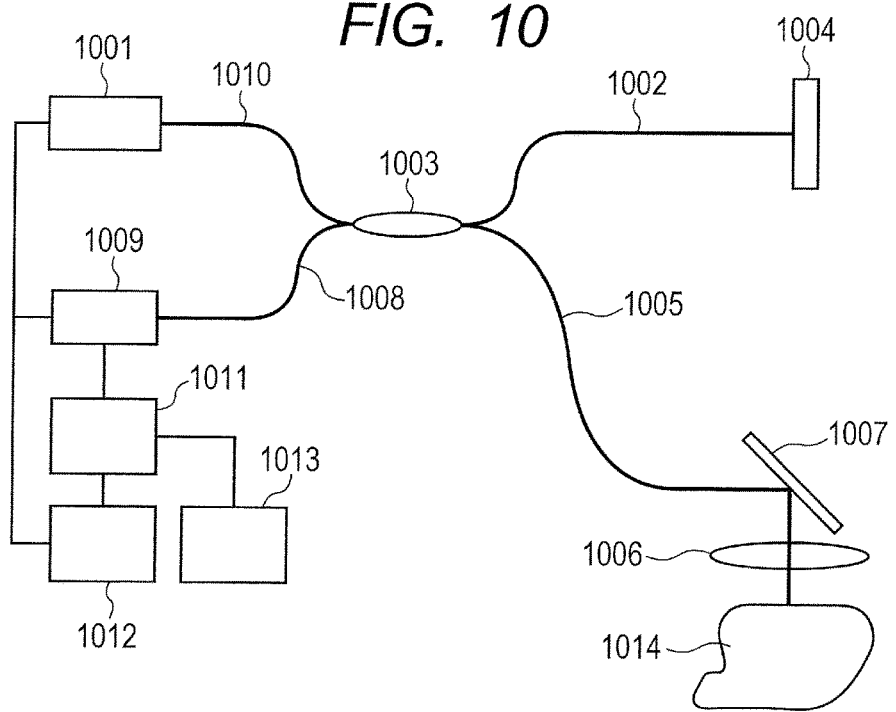
FIG. 10 is a diagram illustrating an exemplary configuration of an OCT apparatus including the SLD according to the embodiment of the present invention.
Figure 11A:
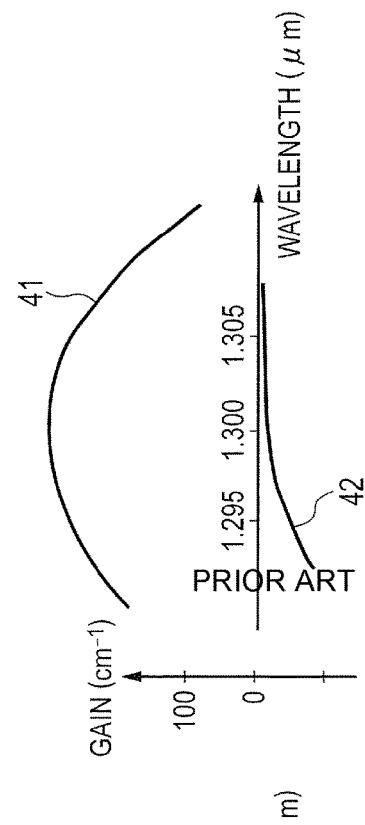
FIG. 11A is a graph showing a gain shape of a semiconductor laser element according to a conventional example described in Patent Literature 1.
Figure 11C:
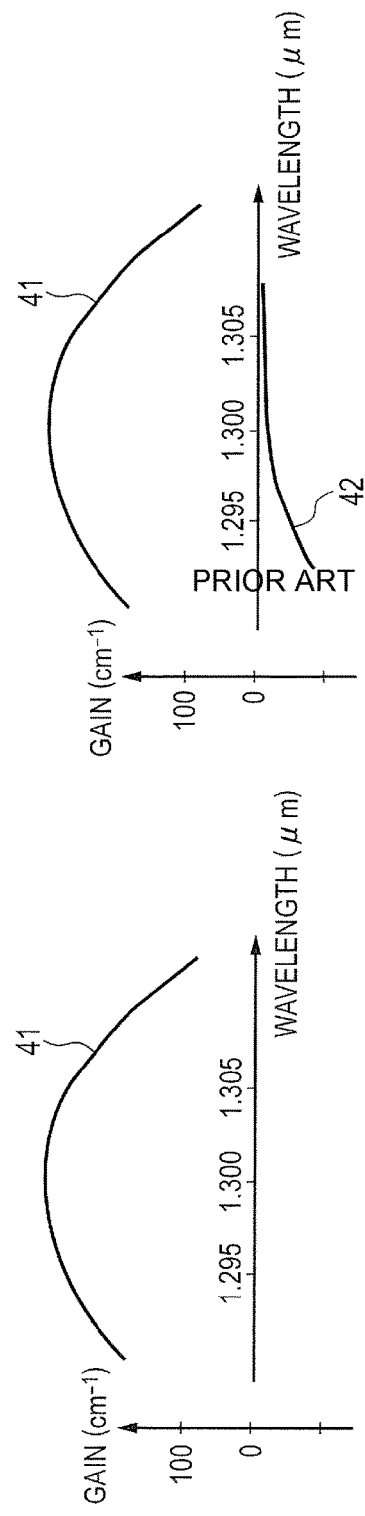
FIG. 11C is a graph showing a spectrum shape of a semiconductor laser element according to an example described in Patent Literature 1.
Figure 11B:
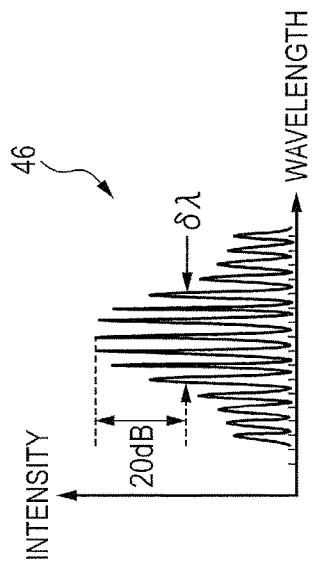
FIG. 11B is a graph showing a spectrum shape of the semiconductor laser element according the conventional example described in Patent Literature 1.
Figure 11D:
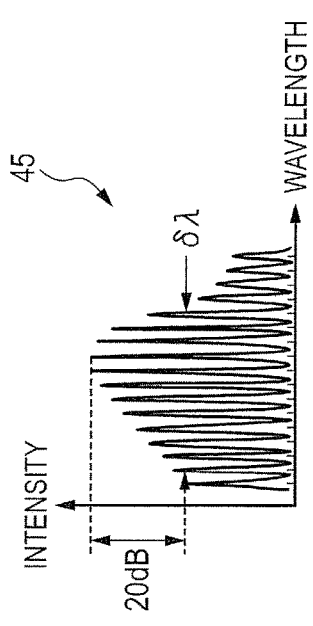
FIG. 11D is a graph showing a spectrum shape of the semiconductor laser element according to the example described in Patent Literature 1.
Figure 12:
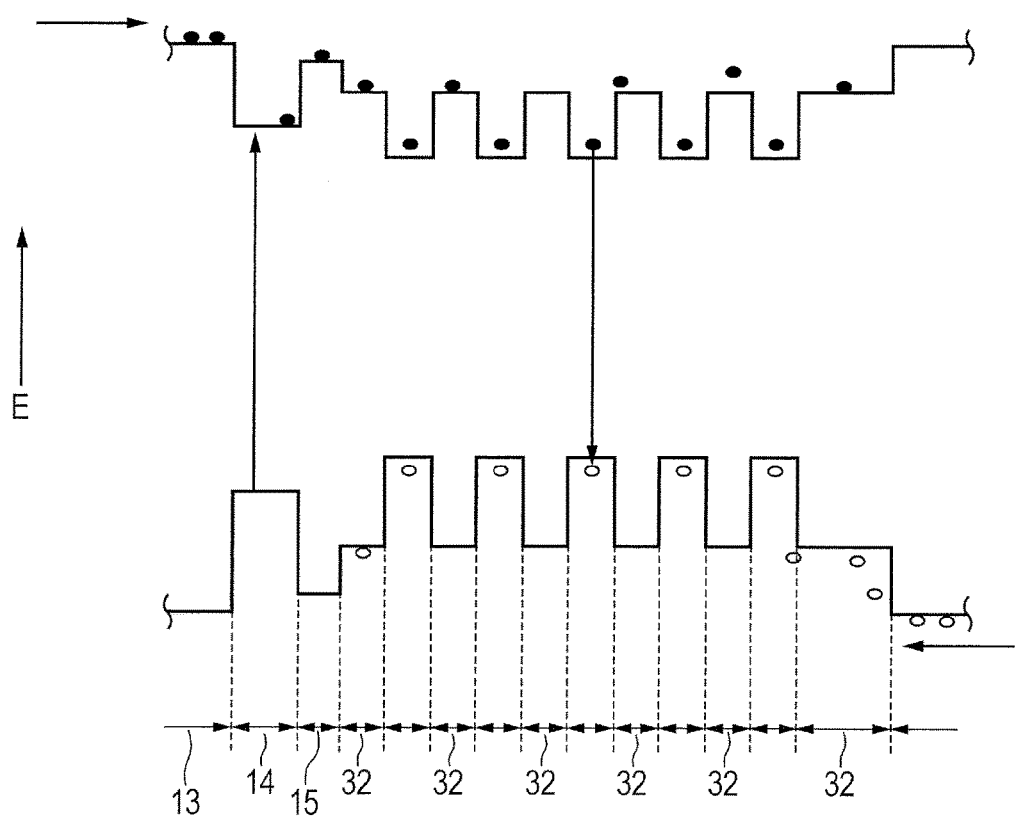
FIG. 12 is a band diagram showing one configuration of the vicinity of an active layer in the semiconductor laser element according to the example described in Patent Literature 1.

FIG. 10 is a schematic diagram of the OCT apparatus according to this embodiment.

The OCT apparatus of FIG. 10 includes a light source part (1001, etc.) for irradiating an analyte with light, an analyte measuring part (1007, etc.) for transmitting reflected light from an analyte part, and a reference part (1002, etc.) for irradiating a reference mirror with light and transmitting reflected light from the reference mirror.

Further, the OCT apparatus includes an interference part (1003, etc.) for causing two reflected lights to interfere with each other, a light detecting part (1009, etc.) for detecting the interference light obtained from the interference part, and an image processing part (1011, etc.) for performing image processing (obtaining a tomographic image) based on the light detected by the light detecting part.

Each component is described below.

The light source part includes an SLD light source 1001 and a light source control device 1012 for controlling the SLD light source 1001, and the SLD light source 1001 is connected to a fiber coupler 1003 forming the interference part through an optical fiber 1010 for light irradiation.

The fiber coupler 1003 in the interference part is formed of a coupler are a single mode type in a wavelength band of the SLD light source 1001, and various fiber couplers are formed of 3 dB couplers.

A reflective mirror 1004 is connected to a reference light optical path fiber 1002 to form the reference part, and the reference light optical path fiber 1002 is connected to the fiber coupler 1003.

An examination light optical path fiber 1005, an irradiation light-collecting optical system 1006, and an irradiation position scanning mirror 1007 form a measurement part, and the examination light optical path fiber 1005 is connected to the fiber coupler 1003. In the fiber coupler 1003, backscattered light generated from an inside and a surface of an object to be examined 1014 and return light from the reference part interfere with each other to form interference light.

The light detecting part is formed of a light-receiving fiber 1008 and a photodetector 1009 and guides the interference light generated in the fiber coupler 1003 to the photodetector 1009. The light received by the photodetector 1009 is converted into a spectrum signal by a signal processing device 1011, and the spectrum signal is further subjected to Fourier transformation, with the result that depth information of the object to be examined 1014 is acquired. The acquired depth information is displayed on an image output monitor 1013 as a tomographic image.

In this case, the signal processing device 1011 can be formed of a personal computer or the like, and the image output monitor 1013 can be formed of a display screen of a personal computer, or the like.

The light source control device 1012 is connected to the signal processing device 1011 for also controlling a driving signal or the like of the irradiation position scanning mirror 1007, and controls the SLD light source 1001 in synchronization with the drive of the irradiation position scanning mirror 1007.

For example, when the light source described above is used as the SLD light source 1001 of this embodiment, the SLD light source 1001 is capable of acquiring information in a wide band. Therefore, information on a tomographic image with a high depth resolution can be acquired at high speed.

Further, the intensity at a wavelength of 790 nm or less where the sensitivity of an eyeball becomes high is low, and hence more accurate measurement can be performed.

The OCT apparatus is useful for capturing tomographic images in ophthalmology, dentistry, dermatology, etc. Note that, although an example of the OCT apparatus is described in this embodiment, the present invention is not limited thereto and can be used as a light source of an OCT apparatus of another system.

EXAMPLES

Examples of the present invention are described below.

Example 1

As Example 1, an exemplary configuration of a super luminescent diode (SLD) to which the present invention is applied is described with reference to FIGS. 6A and 6B.

In the SLD of this example, as a device configuration in which only light intensity on a short wavelength side is decreased in an emission spectrum, a quantum well layer for absorption is disposed in a cladding layer.

Figure 6A:
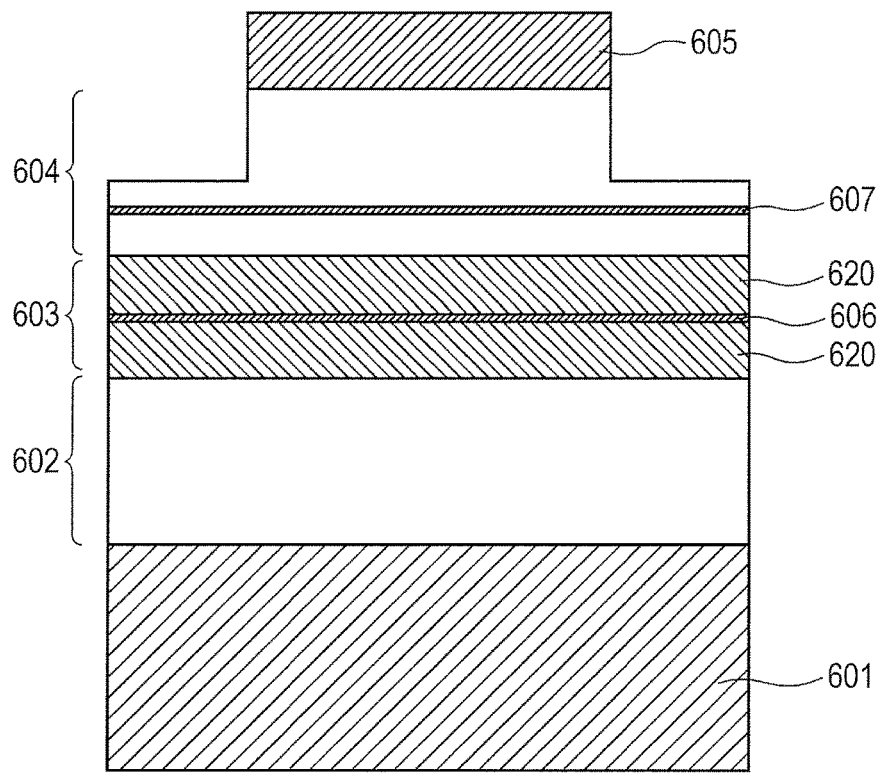
FIG. 6A is a view illustrating an exemplary configuration of an SLD according to Example 1 of the present invention.

FIG. 6A illustrates a layer configuration of the SLD according to this example.

As illustrated in FIG. 6A, an n-doped InP substrate is used for a substrate 601, and n-doped InP is used for a lower cladding layer 602.

Further, an emitting layer 606 made of $InGaAs_{0.7}P$ and barrier layers 620 made of $InGaAs_{0.35}P$ are used for an active layer 603. P-doped InP is used for an upper cladding layer 604, and p-doped InP is used for a contact layer 605. The thickness of the emitting layer 606 is set to 8 nm.

As a light absorbing layer 607, an $InGaAs_{0.6}P$ quantum well layer having a thickness of 8 nm is disposed in the upper cladding layer 604.

The light absorbing layer 607 is positioned at a distance of 50 nm from the interface between the active layer 603 and the upper cladding layer 604.

Figure 6B:
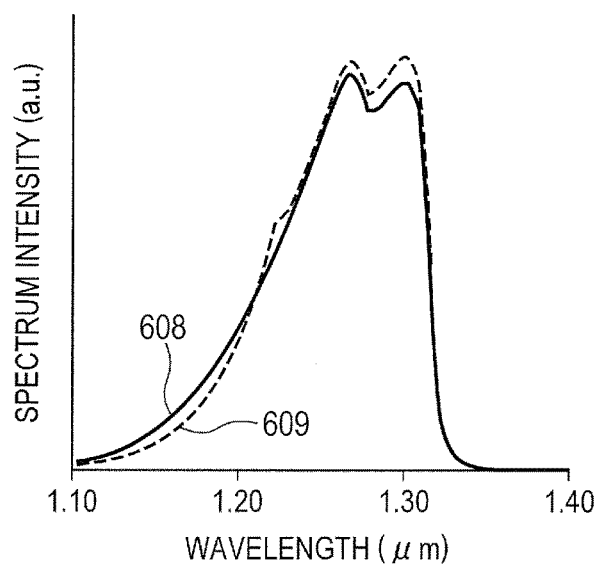
FIG. 6B is a graph showing the exemplary configuration of the SLD according to Example 1 of the present invention.

FIG. 6B shows an emission spectrum in the above-mentioned layer configuration.

A solid line 608 represents the case where there is no light absorbing layer 607 as a comparative example, and a dotted line 609 represents the case where the light absorbing layer 607 is provided as this example.

It is understood from FIG. 6B that, by providing the light absorbing layer 607, intensity on a short wavelength side decreases although no decrease in intensity is found in the vicinity of a center wavelength.

The intensity at a wavelength of 1.15 μm was decreased by about 35% due to the provision of the light absorbing layer 607. Further, a change in half-maximum width in this case was about 1%.

By providing the light absorbing layer 607 in the upper cladding layer 604, only intensity on a short wavelength side can be decreased without changing a spectrum shape substantially.

Example 2

As Example 2, an exemplary configuration of an SLD different from that of Example 1 is described with reference to FIG. 7. This example is directed to the configuration in which a light absorbing part is formed of multiple light absorbing layers.

In the SLD of this example, as a device configuration in which only light intensity on a short wavelength side is decreased in an emission spectrum, two light absorbing layers are provided in a cladding layer.

Figure 7:
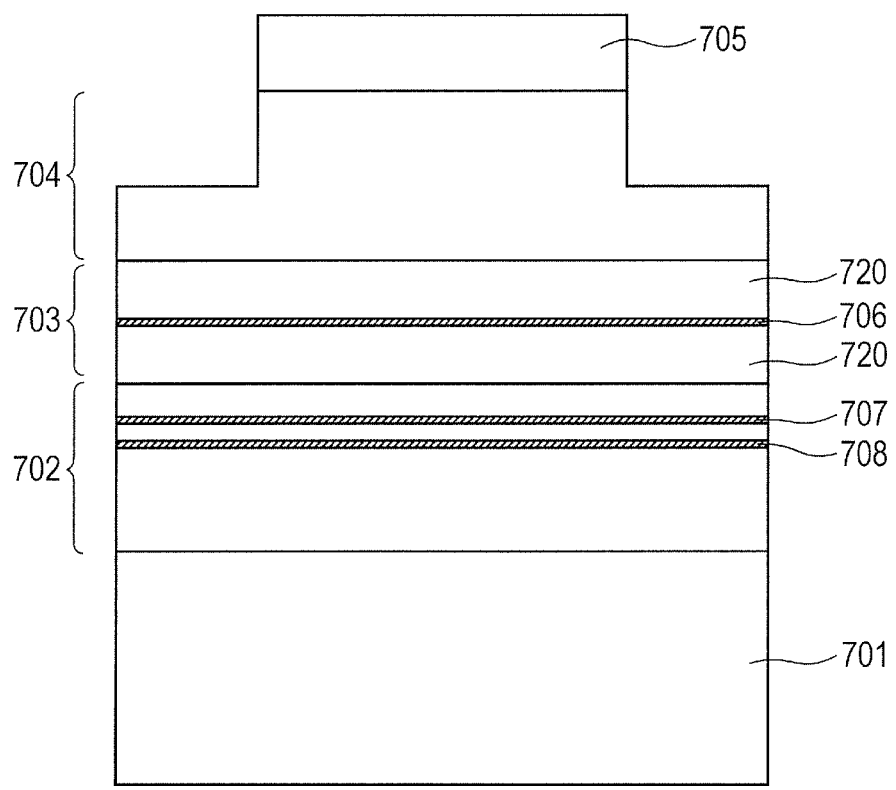
FIG. 7 is a view illustrating an exemplary configuration of an SLD according to Example 2 of the present invention.

As illustrated in FIG. 7, in the SLD according to this example, an n-doped GaAS substrate is used for a substrate 701, and n-doped $Al_{0.5}GaAs$ is used for a lower cladding layer 702.

Further, an emitting layer 706 made of $In_{0.07}GaAs$ and barrier layers 720 made of $Al_{0.2}GaAs$ are used for an active layer 703. P-doped $Al_{0.5}GaAs$ is used for an upper cladding layer 704, and p-doped GaAs is used for a contact layer 705. The thickness of the emitting layer 706 is set to 8 nm. As light absorbing layers 707 and 708, a GaAs quantum well layer having a thickness of 6 nm is disposed in the lower cladding layer 702. The light absorbing layers 707 and 708 are positioned at a distance of 30 nm and 50 nm from the interface between the active layer 703 and the lower cladding layer 702, respectively.

When an emission spectrum in the above-mentioned configuration was compared to an emission spectrum in the case where no light absorbing layer was provided, it was found that intensity was not decreased in the vicinity of a center wavelength and a half-maximum width was not reduced when the light absorbing layer was provided.

The intensity at a wavelength of 790 nm was decreased by about 66%. In the same structure, the intensity was decreased by about 39% in the case where one light absorbing layer was provided at a position of 30 nm from the interface between the active layer 703 and the lower cladding layer 702, and the intensity was decreased by about 38% in the case where one light absorbing layer was provided at a position of 50 nm from the interface between the active layer 703 and the lower cladding layer 702.

In this example, the case where two light absorbing layers 707 and 708 are provided on an n-side from the active layer 703 is described. However, the present invention is not limited thereto. Three or more light absorbing layers may be provided, multiple light absorbing layers may be provided in a p-side cladding layer, or light absorbing layers may be provided in both n-side and p-side cladding layers.

By providing the multiple light absorbing layers in the cladding layer, only intensity on a short wavelength side can be decreased more than the case of providing one layer without changing a spectrum shape substantially.

Example 3

As Example 3, an exemplary configuration of an SLD different from that of above-mentioned respective examples is described with reference to FIGS. 8A to 8B.

In the SLD of this example, the doping concentration on the periphery of a quantum well layer serving as a light absorbing part is set to be lower than that of its surrounding area in a cladding layer.

Figure 8A:
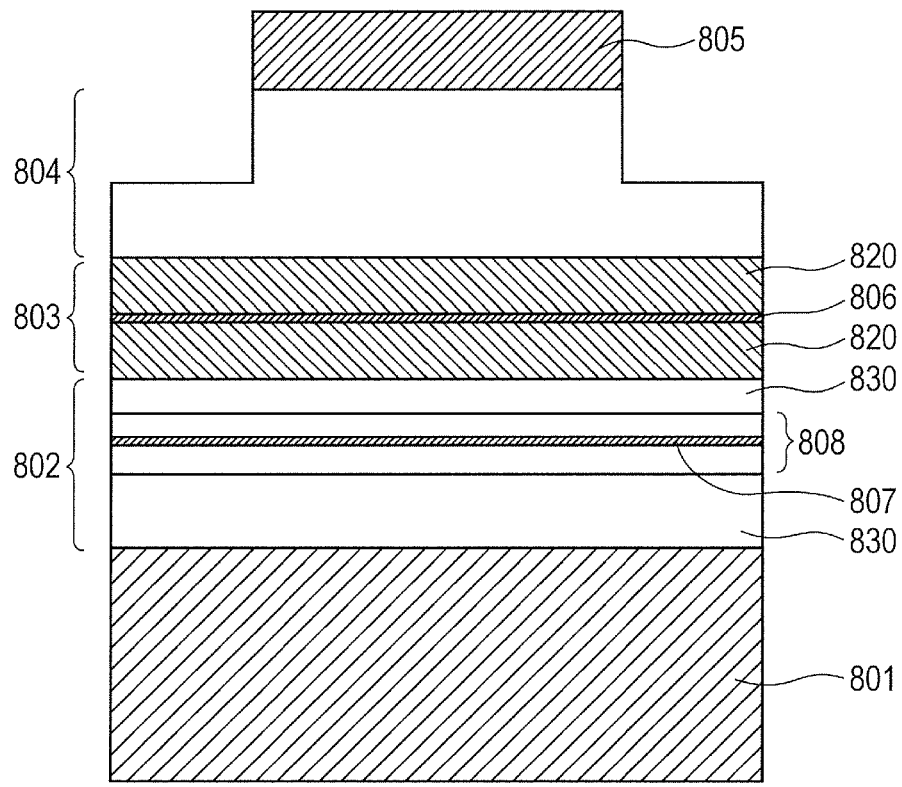
FIG. 8A is a view illustrating an exemplary configuration of an SLD according to Example 3 of the present invention.

In FIG. 8A, a light absorbing part 807 is disposed in a lower cladding layer 802, and further the doping concentration of layers 808 on the periphery of the light absorbing part 807 is lower than that of layers 830 adjacent to the layers 808 on the periphery of the light absorbing part 807 in the lower cladding layer 802.

In this example, the doping concentration of the layers 808 on the periphery of the light absorbing part 807 is set to be lower by two orders of magnitude than that of the layers 830 adjacent to the layers 808. Further, a region having a low doping concentration is set to extend upward and downward respectively by 20 nm from the light absorbing part 807.

Figure 8B:
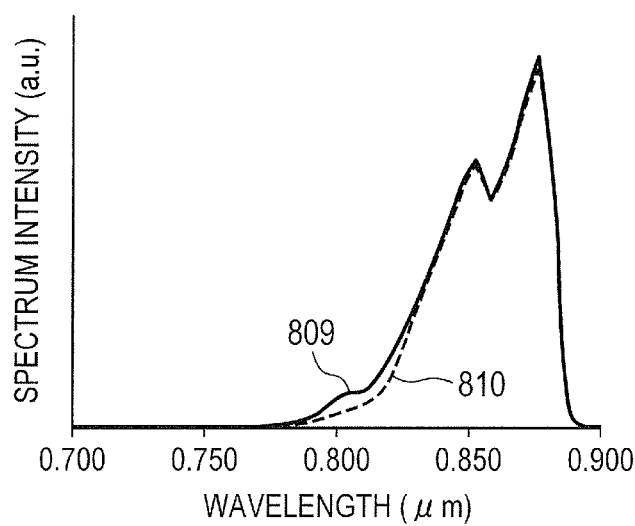
FIG. 8B is a graph showing the exemplary configuration of the SLD according to Example 3 of the present invention.

FIG. 8B shows a spectrum in the case where an emitting layer 806 is made of $In_{0.07}GaAs$ having a thickness of 8 nm, upper and lower barrier layers 820 are made of $Al_{0.2}GaAs$ each having a thickness of 20 nm, a lower cladding layer 802 is made of n-doped $Al_{0.5}GaAs$, and a light absorbing part 807 is made of GaAs having a thickness of 6 nm.

The doping concentration of the lower cladding layer 802 is $1.0\times10^{18}$ cm$^{-1}$. The layers 808 on the periphery of the light absorbing part 807 are made of n-doped $Al_{0.5}GaAs$ and have a doping concentration of $1.0\times10^{16}$ cm$^{-1}$, extending from the light absorbing part 807 upward and downward by 20 nm respectively. Further, the light absorbing part 807 is disposed at a position of 50 nm from the interface between the active layer 803 and the lower cladding layer 802.

Compared to a solid line 809 representing the case where the doping concentration of the layers 808 on the periphery of the light absorbing part 807 is not changed, intensity at a wavelength of 790 nm is decreased by about 42% in a dotted line 810 representing the case where the doping concentration of the layers 808 on the periphery of the light absorbing part 807 is set to be lower by two orders of magnitude than that of the surrounding area.

In this example, the example where the light absorbing part 807 is disposed on an n-side is described. However, the present invention is not limited thereto, and the light absorbing part 807 and its surrounding region whose doping concentration is decreased may be disposed on a p-side or on both the p-side and the n-side.

Example 4

Figure 9:
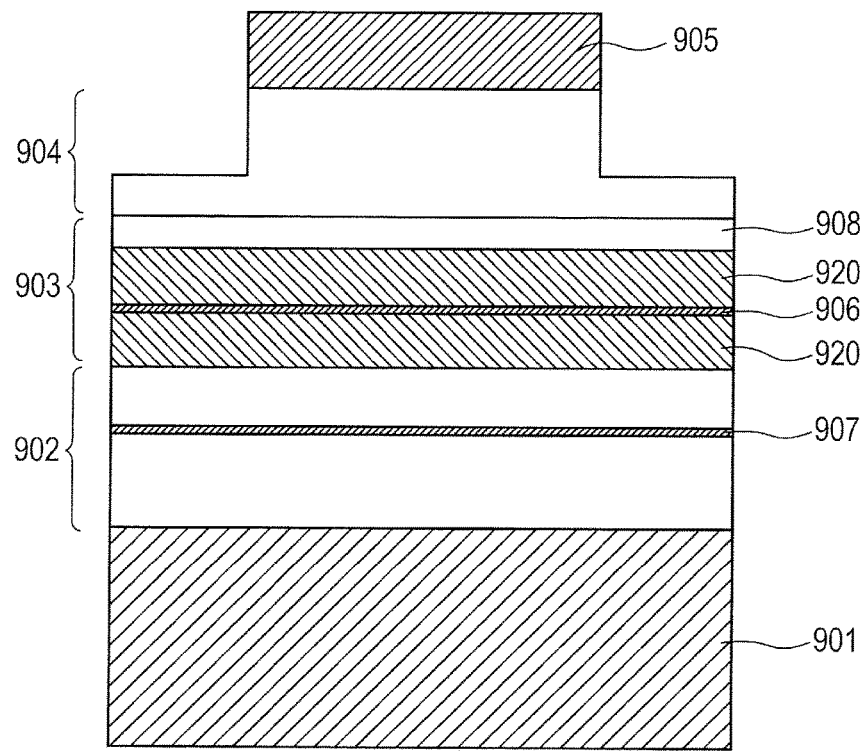
FIG. 9 is a view illustrating an exemplary configuration of an SLD according to Example 4 of the present invention.

As Example 4, an exemplary configuration in which the light intensity distribution is more concentrated on the side of the light absorbing layer through use of an optical guide layer is described with reference to FIG. 9.

In this example, a light absorbing part 907 is disposed in a lower cladding layer 902, and further an active layer 903 includes an optical guide layer 908. The optical guide layer 908 which is a region from the interface with above an emitting layer 906 to the interface with an upper cladding layer 904 has a refractive index lower than that of the remaining region of the active layer 903.

In the active layer 903, the thicknesses of the emitting layer 906 made of $In_{0.07}GaAs$ and each of barrier layers 920 made of $Al_{0.2}GaAs$ are set to 8 nm and 20 nm, respectively. A portion having a thickness of 10 nm of the active layer 903 on the upper cladding layer 904 side is replaced by $Al_{0.3}GaAs$, and this portion is used as the optical guide layer 908.

In this case, when the light absorbing part 907 is disposed in the lower cladding layer 902 made of $Al_{0.5}GaAs$ at a position of 50 nm from the interface between the lower cladding layer 902 and the active layer 903, the spectrum intensity is decreased by about 3% at a wavelength of 790 nm, compared to the case where no optical guide layer 908 is provided.

In this example, the case where the optical guide layer 908 is disposed in the active layer 903 is described. However, the present invention is not limited thereto, and the optical guide layer 908 may have any configuration as long as the light intensity distribution can be concentrated on the light absorbing part 907 side.

More specifically, a region having a refractive index lower than that of a surrounding barrier region may be provided in the barrier region on an opposite side of the light absorbing part 907 with respect to the emitting layer 906. Alternatively, a region having a refractive index higher than that of a surrounding cladding region may be provided in the cladding layer on the same side of the light absorbing part 907 with respect to a quantum well layer for emitting light.

Light having intensity at a short wavelength can be absorbed more effectively through use of the optical guide layer 908.

Example 5

Figure 13:
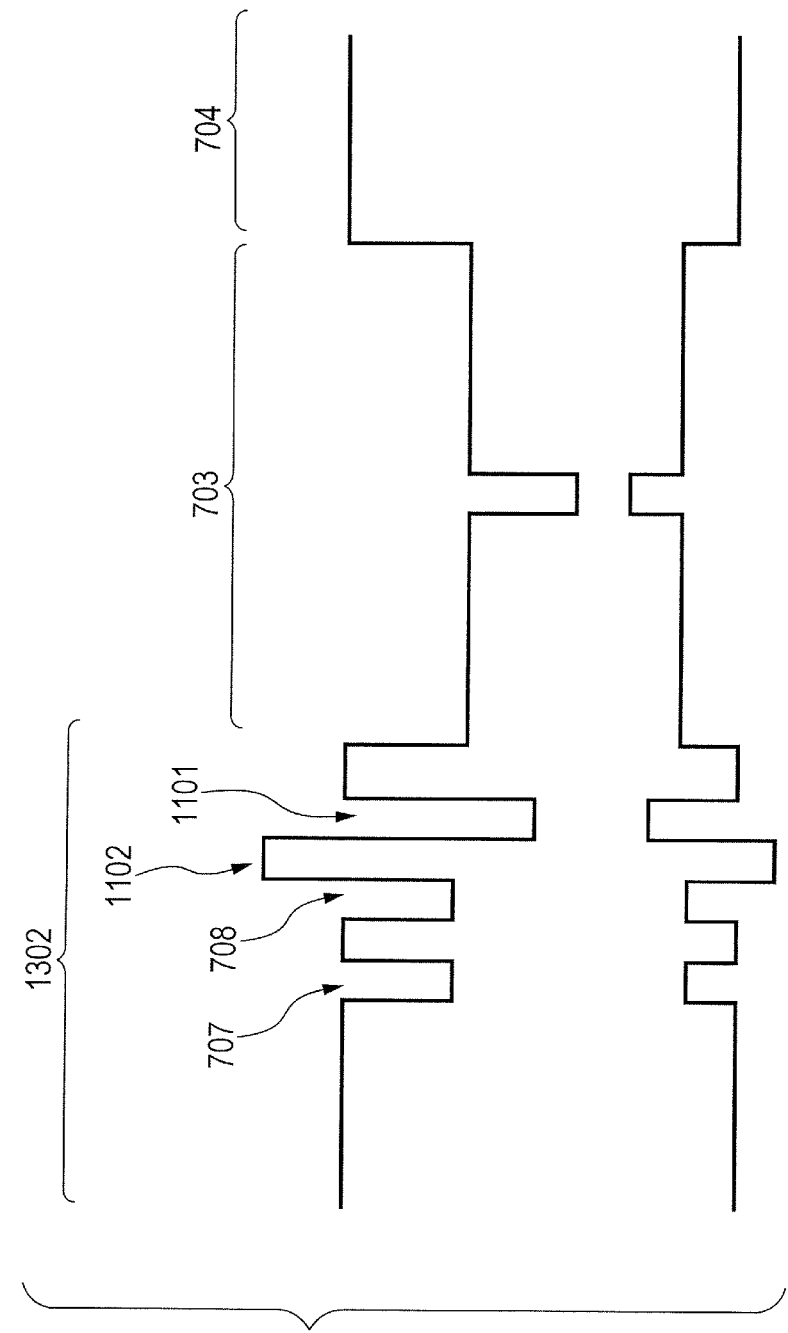
FIG. 13 is a band diagram of a semiconductor layer structure of an SLD according to Example 5 of the present invention.

In this example, the active layer 703, the cladding layers 702 and 704, the light absorbing parts 707 and 708, and the substrate 701 which are the same as those of Example 2 are used. FIG. 13 shows a band diagram of a semiconductor layer structure in the vicinity of the emitting layer in this example. Example 5 has a difference from Example 2 that a carrier consuming layer 1101 having a bandgap smaller than that of the cladding layer 1302 and a barrier layer 1102 having a bandgap larger than that of the cladding layer 1302 are provided between the active layer 703 and the light absorbing parts 707 and 708. N-doped $Al_{0.5}GaAs$ which is the same as the cladding layer 702 used in Example 2 is used for the cladding layer 1302. The other parts have the same structure as that of Example 2. Therefore, the effect obtained by the above-mentioned difference is described below.

This example describes a mechanism capable of further suppressing the inflow of carriers into the light absorbing parts 707 and 708 and light emission by providing the carrier consuming layer 1101 and the barrier layer 1102 in addition to the suppression of light emission by providing the light absorbing parts 707 and 708 in a doped layer. First, the effect of providing the barrier layer 1102 having a bandgap larger than that of the cladding layers 1302 is described. In this case, in the same way as in conventional semiconductor lasers, a layer having a large bandgap is provided so as to suppress overflow of carriers. As a result, a bandgap barrier is formed. Then, in order for carriers to overpass the barrier, energy corresponding to the difference caused by the barrier is required. However, there are few carriers having such high energy, and hence, most of the carriers are prevented from proceeding further by the barrier.

Next, the effect of providing the carrier consuming layer 1101 in the cladding layer 1302 having a bandgap smaller than that of the cladding layer 1302 is described. Minority carriers leaking from the non-doped emitting layer to the cladding layers 1302 flow into the carrier consuming layer 1101 having a small bandgap. Then, the minority carriers are confined in the carrier consuming layer 1101 for a long period of time because the carrier consuming layer 1101 is a region having a small energy potential. Therefore, a probability that the minority carriers are recombined increases, and the minority carriers are consumed in the carrier consuming layer 1101.

It is preferred that the above-mentioned two layers, that is, the barrier layer 1102 and the carrier consuming layer 1101 be provided in the order stated in this example. By providing those two layers in such a manner, a configuration is obtained in which the barrier between the carrier consuming layer 1101 and the barrier layer 1102 can be maximized, and the overflow suppression of the carriers by the large barrier and the consumption of the carriers prior to the overflow suppression can be combined.

Further, the bandgap of the carrier consuming layer 1101 is in the vicinity of the shortest wavelength of an emission spectrum. Light emission caused by the recombination of carriers occurs in the carrier consuming layer 1101. Therefore, when this wavelength is originally positioned in a wavelength band from which light emission is expected, light emission therefrom can also be used. Further, the bandgap is in an end of a short wavelength, and hence light having a wavelength longer than that of the end of the short wavelength is not influenced by basic absorption between the bandgaps of the carrier consuming layer 1101. Therefore, it is preferred that the bandgap of the carrier consuming layer 1101 be in the vicinity of the end of a short wavelength side in a wavelength band to be used.

Advantageous Effects of Invention

According to the present invention, it is possible to realize the photonic device in which emission intensity in a short wavelength region is suppressed even in the case of increasing carrier injection density so as to obtain a wide spectrum half-maximum width as well as a high output.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a national stage application of PCT/JP2013/080054, filed on Oct. 30, 2013, which claims the benefit of Japanese Patent Application No. 2012-244344, filed on Nov. 6, 2012. The contents of the aforementioned applications are incorporated herein by reference in their entirety.

REFERENCE SIGNS LIST

101: substrate
102: lower cladding layer
103: active layer
104: upper cladding layer
105: contact layer
106: emitting layer
107: light absorbing part

The invention claimed is:
1. A photonic device comprising:
a first cladding layer;
a second cladding layer; and
an active layer including an emitting layer and a barrier layer and being provided between the first cladding layer and the second cladding layer, the emitting layer emitting light in a spectrum having a center wavelength $\lambda c$ and a spectrum half-maximum width $\Delta\lambda$,
wherein at least one of the first cladding layer and the second cladding layer includes a light absorbing part for absorbing light having a wavelength of λs or less represented by the following Expression (1):

$$\lambda s < (\lambda c - (\Delta\lambda/2)) \qquad (1),\text{ and}$$

wherein the light absorbing part comprises a light absorbing layer, the light emitted from the emitting layer has a spectrum center wavelength of 830 to 870 nm, and the light absorbing layer absorbs at least light having a wavelength of 790 nm or less.

2. The photonic device according to claim 1, wherein the light absorbing part comprises a quantum well layer.

3. The photonic device according to claim 2, wherein:
the light absorbing part comprises multiple light absorbing layers; and
the multiple light absorbing layers are disposed in at least one of the first cladding layer and the second cladding layer.

4. The photonic device according to claim 2, wherein:
the first cladding layer and the second cladding layer each have a doped configuration; and
a doping concentration of a layer on a periphery of the light absorbing part, which is positioned in the doped cladding layer, is lower than a doping concentration of a layer adjacent to the layer on the periphery of the light absorbing part.

5. The photonic device according to claim 1, further comprising a layer having a refractive index different from a refractive index of a periphery, the layer being disposed in at least one of the barrier layer, and the first cladding layer and the second cladding layer in which the light absorbing layer is disposed,
wherein a light intensity distribution from the emitting layer is configured so as to increase in a place where the light absorbing layer is positioned in the at least one of the first cladding layer and the second cladding layer.

6. The photonic device according to claim 1, wherein:
the emitting layer comprises multiple semiconductor layers;
at least one of the first cladding layer and the second cladding layer is doped; and
the photonic device further comprises a carrier consuming layer having a bandgap which is smaller than a bandgap of the first cladding layer and the second cladding layer and which is larger than a bandgap of a layer having a smallest bandgap among the multiple semiconductor layers, the carrier consuming layer being provided in the doped cladding layer and between the emitting layer and the light absorbing layer.

7. The photonic device according to claim 6, wherein:
the carrier consuming layer and a barrier layer having a bandgap larger than the bandgap of the doped cladding layer are disposed in the doped cladding layer and between the emitting layer and the light absorbing layer; and
the active layer, the carrier consuming layer, and the barrier layer are provided in the stated order.

8. An optical coherence tomography apparatus comprising:
a light source part including the photonic device according to claim 1;
an analyte measuring part for irradiating an analyte with light from the light source part and transmitting reflected light from the analyte;
a reference part for irradiating a reference mirror with the light from the light source part and transmitting reflected light from the reference mirror;
an interference part for causing reflected light from the analyte measuring part and reflected light from the reference part to interfere with each other;
a light detecting part for detecting interference light from the interference part; and
an image processing part for obtaining a tomographic image of the analyte based on the interference light detected by the light detecting part.

9. A photonic device comprising:
a first cladding layer;
a second cladding layer; and
an active layer including an emitting layer and a barrier layer and being provided between the first cladding layer and the second cladding layer, the emitting layer emitting light in a spectrum having a center wavelength λc and a spectrum half-maximum width Δλ,
wherein at least one of the first cladding layer and the second cladding layer includes a light absorbing part for absorbing light having a wavelength of λs or less represented by the following Expression (1):

$$\lambda s < (\lambda c - (\Delta\lambda/2)) \qquad (1),\text{ and}$$

wherein the light absorbing part is provided at a distance of 30 nm or more and 150 nm or less from the emitting layer.

10. The photonic device according to claim 9, wherein the light absorbing part is provided at a distance of 40 nm or more and 70 nm or less from the emitting layer.

11. The photonic device according to claim 9, wherein the light absorbing part comprises a GaAs layer.

12. The photonic device according to claim 11, wherein the GaAs layer has a thickness of 5-6 nm.

* * * * *